US012385081B2

(12) United States Patent
Herrera et al.

(10) Patent No.: US 12,385,081 B2
(45) Date of Patent: Aug. 12, 2025

(54) DETECTION OF PATHOGENS IN WASTEWATER

(71) Applicant: Bio-Rad Laboratories, Inc., Hercules, CA (US)

(72) Inventors: Monica Herrera, Dublin, CA (US); Josh Shinoff, Emeryville, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 952 days.

(21) Appl. No.: 17/507,472

(22) Filed: Oct. 21, 2021

(65) Prior Publication Data

US 2022/0119896 A1 Apr. 21, 2022

Related U.S. Application Data

(60) Provisional application No. 63/094,753, filed on Oct. 21, 2020.

(51) Int. Cl.
*C12Q 1/6806* (2018.01)
*C12N 15/10* (2006.01)
*C12Q 1/6844* (2018.01)

(52) U.S. Cl.
CPC ....... *C12Q 1/6806* (2013.01); *C12N 15/1017* (2013.01); *C12Q 1/6844* (2013.01)

(58) Field of Classification Search
None
See application file for complete search history.

(56) References Cited

U.S. PATENT DOCUMENTS

| 8,257,568 B1 | 9/2012 | Simmons et al. |
| 2007/0160983 A1 | 7/2007 | Paul, III et al. |
| 2009/0101575 A1* | 4/2009 | Alburty ............... C12Q 1/24 210/717 |
| 2015/0038356 A1* | 2/2015 | Karlin-Neumann ........ C12Q 1/6827 435/5 |

FOREIGN PATENT DOCUMENTS

| WO | 2004/094667 A2 | 11/2004 |
| WO | 2008/151093 A1 | 12/2008 |

OTHER PUBLICATIONS

Rački, N., Dreo, T., Gutierrez-Aguirre, I. et al. Reverse transcriptase droplet digital PCR shows high resilience to PCR inhibitors from plant, soil and water samples. Plant Methods 10, 42 (2014). https://doi.org/10.1186/s13007-014-0042-6 (Year: 2014).*
Chuang, C., Chiou, S., Liang, L., & Chen, W. (n.d.). Short Report: Detection of Japanese Encephalitis Virus in Mouse Peripheral Blood Mononuclear Cells Using an in Situ Reverse Transcriptase-Polymerase Chain Reaction. Am. Jour. of Trop. Med. and Hyg., 69(6), 648-651. 2003. (Year: 2003).*
Peccia, J. et al.; "Measurement of SARS-CoV-2 RNA in wastewater tracks community infection dynamics"; *Nature Biotechnology*; vol. 38; Oct. 2020; pp. 1164-1167.
Li, N. et al.; "Digital PCR quantification of miRNAs in sputum for diagnosis of lung cancer"; *J Cancer Res Clin Oncol.*; vol. 140; No. 1: Jan. 2014; pp. 145-150.
Rusinol, M. et al.; "Concentration methods for the quantification of coronavirus and other potentially pandemic enveloped virus from wastewater"; *Current Opinion in Environmental Science & Health*; vol. 17; 2020; pp. 21-28.
"Concentrating Pipette"; InnovaPrep LLC; https://www.innovaprep.com/products/concentrating-pipette; as accessed on the internet Jan. 27, 2022; 3 pages.
International Search Report and Written Opinion from PCT/US2021/056057 mailed Jan. 28, 2022; 11 pages.
Extended European Search Report in EP Appln. 21883896.9 mailed Apr. 17, 2025; 10 pages.
Gonzalez, R. et al.; "COVIA-19 surveillance in Southeastern Virginia using wastewater-based epidemiology"; *Water Research*; Elsevier, Amsterdam NL; vol. 186; Aug. 13, 2020; 9 pages.
Racki, N. et al.; "One-step RT-droplet digital PCT: a breakthrough in the quantification of waterborne RNA viruses"; *Analytical and Bioanalytical Chemistry*; vol. 406, No. 3; Nov. 26, 2013; pp. 661-667.
Ahmed, W. et al.; "Detection of SARS-CoV-2 RNA in commercial passenger aircraft and cruise ship wastewater: a surveillance tool for assessing the presence of COVID-19 infected travellers"; *Journal of Travel Medicine*; vol. 27, No. 5; Aug. 20, 2020; pp. 1-11.
Ahmed, W. et al.; "Comparison of virus concentration methods for the RT-qPCR-based recovery of murine hepatitis virus, a surrogate for SARS-CoV-2 from untreated wastewater"; Science of the Total Environment; Elsevier, Amsterdam, NL; vol. 739; Jun. 5, 2020; 9 pages.
Corpuz, M.V.A. et al.; "Viruses in wastewater: occurrence, abundance and detection methods"; *Science of the Total Environment*; Elsevier, Amsterdam, NL; vol. 745; Jul. 19, 2020; 26 pages.
Patel, M. et al.; "Coronavirus (SARS-CoV-2) in the environment: Occurrence, persistence, analysis in aquatic systems and possible management"; *Science of the Total Environment*; Elsevier, Amsterdam, NL; vol. 765; Oct. 2, 2020; 18 pages.
Farkas, K. et al.; "Two-Step Concentration of Complex Water Samples for the Detection of Viruses"; *Methods and Protocols*; vol. 1, No. 3; Sep. 10, 2018; 6 pages.

* cited by examiner

*Primary Examiner* — Thomas J. Visone
*Assistant Examiner* — Katherine A. Willard
(74) *Attorney, Agent, or Firm* — Kilpatrick Townsend and Stockton LLP

(57) ABSTRACT

Methods of concentrating RNA from wastewater and quantifying the RNA by digital amplification are provided.

10 Claims, No Drawings

DETECTION OF PATHOGENS IN WASTEWATER

CROSS-REFERENCE TO RELATED PATENT APPLICATIONS

The present patent application claims benefit of priority to U.S. Provisional Patent Application No. 63/094,753, filed on Oct. 21, 2020, which is incorporated by reference for all purposes.

BACKGROUND OF THE INVENTION

Detection of pathogens in wastewater (e.g., sewage or other effluents originating from human or other animals) can provide useful epidemiological information regarding the prevalence of particular pathogens, allowing for changes in policies or procedures in regulating disease spread. An example of detection of pathogens in wastewater was recently described for the SARS-CoV-2 virus, which causes COVID-19. See, e.g., Peccia et al., *Nature Biotechnology* volume 38, pages 1164-1167 (2020).

Wastewater contains a large number of inhibitors of the tools of molecular biology manipulation. Notably, polymerase activity can be harmed by inhibitors present in wastewater. Previously this issue has been overcome by RNA extraction, in which RNA in wastewater is separated from other components by organic (e.g., phenol) extraction.

BRIEF SUMMARY OF THE INVENTION

Aspects of the methods can be found elsewhere herein. In some embodiments, methods of detecting RNA in wastewater are provided. In some embodiments, the method comprises providing a sample comprising RNA in wastewater; concentrating RNA in the sample (e.g., at least 100 fold) to form a concentrated sample, wherein the concentrating removes particulates from the sample; dividing the concentrated sample into a plurality of partitions; performing reverse transcription polymerase chain reaction (RT-PCR) in the partitions to amplify the target RNA, if present, to generate an amplified cDNA; and detecting the presence or absence of amplified cDNA in the partitions, wherein the method does not comprise RNA extraction.

In some embodiments, the method comprises providing a sample comprising virions comprising RNA in wastewater; concentrating virions in the sample at least 100 fold to form a concentrated sample, wherein the concentrating removes particulates from the sample; dividing the concentrated sample into a plurality of partitions; performing reverse transcription polymerase chain reaction (RT-PCR) in the partitions to amplify the target RNA, if present, from the virions to generate an amplified cDNA; detecting the presence or absence of amplified cDNA in the partitions.

In some embodiments, the method further comprises quantifying the target RNA or virion number in the wastewater based on the number of partitions containing detected amplified cDNA.

In some embodiments, the concentrating comprises tangential flow concentration. In some embodiments, the tangential flow comprises flowing the sample by hollow fiber filters and extracting captured particles with a foamed wash buffer.

In some embodiments, the partitions are droplets or microwells.

In some embodiments, the plurality comprises at least 100, 1000, or 10000 partitions.

In some embodiments, the partitions comprise a fluorescent probe that specifically hybridizes to the amplified cDNA during the detecting. In some embodiments, the fluorescent probe is an intercalating dye. In some embodiments, the fluorescent probe is a hydrolysis probe or a molecular beacon.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methyl- ations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis,* and *Thermotoga maritime,* or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

DETAILED DESCRIPTION OF THE INVENTION

Provided herein is a method of detecting RNA in wastewater while avoiding (omitting) an RNA extraction step, thereby greatly shortening the time and steps required to detect RNA in wastewater. The inventors have determined that instead of extraction, the RNA (which can be contained in intact virions) can be concentrated and subsequently amplified in partitions. The combination of concentration and then dilution of remaining inhibitors that results from amplification in partitions with limited sample (and thus inhibitor) concentration allows for an efficient method of detection of RNA from wastewater. Thus, the method allows for a very fast and efficient process allowing for concentration of RNA (including for example virions comprising the RNA) without an RNA extraction method or for example PEG precipitation.

The method can be used with any wastewater source where it is desired to detect RNA. Waste water can include, for example, treated or untreated sewage and rain runoff. For example, wastewater can be obtained from a sewage treatment plant. By detecting RNA, e.g., from pathogens or non-pathogens, e.g., virions, one can determine the presence and quantity of RNA in the water, indicating the prevalence of the source of the RNA (e.g., pathogen or non-pathogen) in the population contributing to the wastewater. For example, a wastewater plant services sewage from a population and thus by measuring RNA from a pathogen in the wastewater one can determine the prevalence of the pathogen in that population.

As noted above, in some embodiments, wastewater is not submitted to an RNA extraction step, e.g., a step of organic phase extraction that generates an organic and separate aqueous phase. Such RNA extractions typically employ phenol. Merely as an example, Qiagen's RNeasy PowerSoil Total RNA method employs a phenol/chloroform extraction step. By not including an extraction step, the method can in some embodiments result in intact virions in the subsequent partition step, whereas extraction removes or destroys intact virions.

In some embodiments, the method can comprise, consist essentially of, or consist of providing the waste water sample, concentrating the sample as described herein, optionally diluting the concentrated sample, and then partitions the resulting concentrated (and optionally diluted) sample and performing amplification of the target RNA(s) in the partitions and detecting the presence or absence of amplification in the partitions. The optionally dilution of the concentrate can include, for example, dilution of the concentrate, e.g., by 1×-2× or 1-10×, with a buffer that will not interfere with subsequent amplification. In some embodiments, this can further dilute possible inhibitors in the concentrate.

In the methods described herein, a wastewater sample is submitted to a concentration step wherein the RNA (optionally intact virions comprising RNA) is concentrated and at least some particulates are removed. The RNA can be concentrated for example at least 10-fold, $10^2$-fold, $10^3$-fold, $10^4$-fold, $10^4$-fold, or $10^6$-fold. The concentration step should be sufficient to generate a concentrated sample volume sufficiently concentrated with the target RNA such that the concentrated sample can be applied to partition-based detection methods, for example such as digital PCR methods.

In some embodiments, the concentration can comprise applying tangential flow concentration to the wastewater sample. For example, the tangential flow can comprise flowing the sample by hollow fiber filters. In some embodiments, the concentration further comprises extracting captured particles with a foamed wash buffer. In some embodiments, the concentrating comprises flowing a the wastewater sample through a hollow fiber filter to separate an amount of particulates in the sample by trapping the particulates on a feed side of the hollow fiber filter and providing a wash liquid and a water soluble gas under pressure, the wash liquid becoming a foam liquid wash material as the gas is released from under pressure and agitated. In this embodiment, particulates are extracted from the feed side of the hollow fiber filter by flowing the foamed liquid wash material through a fluid path extending from a permeate side of the hollow fiber filter across the hollow fiber filter to the feed side of the hollow fiber filter. A valve that is controlled with a timer to dispense reproducible volumes of foam can be used to controlling foam pressure and valve opening time. A commercial example of such technology is InnovaPrep, which uses a wet foam elution. This technology is also described in U.S. Pat. Nos. 8,110,112 and 8,584,535; 8,758,623; 9,534,989; 9,574,977; and 9,574,977.

Following concentration, the concentrated sample can be partitioned. One or more of cell lysis, first strand synthesis, second strand synthesis, or first and second strand synthesis can be performed in the partitions. In some embodiments, the concentrated sample is partitioned such that the partitions contain a sufficiently low number of copies of a target RNA that measurement of the number of partitions that register as positive for the presence of the RNA can be used to determine the concentration of RNA in the original wastewater sample. Methods of quantification of target nucleic acids in a sample using digital PCR techniques involving amplification in partitions is known. See, e.g., Day E, et al., *Methods*. 2013;59:101-107 and Li et al., *J Cancer Res Clin Oncol*. 2014 January; 140(1): 145-150.

In some embodiments, the concentrated sample is partitioned such that there is at least 20 (e.g., at least 50, 100, 200, 500, 1000) partitions that signal "negative" and at least 20 (e.g., at least 50, 100, 200, 500, 1000) partitions that signal positive. In some embodiments, a majority of the partitions have 0 or 1 copy of a target RNA molecules. Generally conditions can be selected such that statistically relevant information can be generated from digital output of the partitions, as known in digital PCR methods. While in some embodiments, absolute quantity of the parget RNA in the original sample can be determined, in some embodiments, only a relative amount compared for example to a different or earlier sample is needed. Especially in situations where relative change in target RNA between samples is desired, the presence of inhibitors in some partitions should not pose an issue in the resulting data so long as some partitions are generated that contain the target and lack inhibitors such that a signal can be generated in some partitions containing the target RNA. In situations in which the amount of inhibitor in the wastewater remains relatively constant between samples but the amount of target RNA changes, a change in target RNA can be detected. This can be sufficient, for example, to report of trends in pathogen contamination in wastewater over time or between locations.

Methods and compositions for partitioning a sample are described, for example, in published patent applications WO 2010/036,352, US 2010/0173,394, US 2011/0092,373, and US 2011/0092,376, the contents of each of which are incorporated herein by reference in the entirety. The plurality of mixture partitions can be in a plurality of emulsion droplets, or a plurality of microwells, etc.

The concentrated sample can be partitioned into a plurality of mixture partitions, optionally cells in the partitions, if present, can be lysed, and first strand synthesis can be performed therein. For example, mRNA can be partitioned into a plurality of mixture partitions and first strand synthesis and second strand synthesis can be performed therein.

In some embodiments, RNA can be partitioned into a plurality of mixture partitions, and then one or more amplification primer(s), probe(s), enzyme(s), oligonucleotides or a combination thereof, can be introduced into the plurality of mixture partitions. Methods and compositions for delivering reagents to one or more mixture partitions include microfluidic methods as known in the art; droplet or microcapsule merging, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

The mixture partitions can be picowells, nanowells, or microwells. The mixture partitions can be pico-, nano-, or micro- reaction chambers, such as pico, nano, or microcapsules. The mixture partitions can be pico-, nano-, or microchannels. The mixture partitions can be droplets, e.g., emulsion droplets.

For digital droplet RT-PCR, an amplification reaction mixture can be prepared. In some embodiments, the amplification reaction mixture comprises one or more target-specific amplification primers. In some embodiments, the amplification mixture further comprises one or more of salts, nucleotides, buffers, stabilizers, reverse transcriptase, DNA polymerase, a detectable agent, and nuclease-free water. Exemplary methods of digital RT-PCR are described in, e.g., Sedlak et al., *J Clin Microbiol* 55:442-449 (2014).

Suitable reverse transcriptases can include for example Superscript II (Life Tech), Superscript III (Life Tech), Superscript IV (Life Tech), Maxima RNAse+ (Thermo), Maxima RNAse-(Thermo), and Sensiscript (Qiagen). Generally, reverse transcriptases typically include eukaryotic RNA polymerases I, II, and III, and bacterial RNA polymerases as well as phage and viral polymerases. RNA polymerases can be DNA-dependent and RNA-dependent. RNA polymerases can have RNAse H+ activity and RNAse H- activity.

In some embodiments, the amplification reaction mixture also comprises a DNA polymerase. DNA polymerases for use in the methods described herein can be any polymerase capable of replicating a DNA molecule. In some embodiments, the DNA polymerase is a thermostable polymerase. Thermostable polymerases are isolated from a wide variety of thermophilic bacteria, such as *Thermus aquaticus* (Taq), *Pyrococcus furiosus* (Pfu), *Pyrococcus woesei* (Pwo), *Bacillus sterothermophilus* (Bst), *Sulfolobus acidocaldarius* (Sac) *Sulfolobus solfataricus* (Sso), *Pyrodictium occultum* (Poc), *Pyrodictium abyssi* (Pab), and *Methanobacterium thermoautotrophicum* (Mth), as well as other species. DNA polymerases are known in the art and are commercially available. In some embodiments, the DNA polymerase is Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, or an active mutant, variant, or derivative thereof. In some embodiments, the DNA polymerase is Taq DNA polymerase. In some embodiments, the DNA polymerase is a high fidelity DNA polymerase (e.g., iProof™ High-Fidelity DNA Polymerase, Phusion® High-Fidelity DNA polymerase, Q5® High-Fidelity DNA polymerase, Platinum® Taq High Fidelity DNA polymerase, Accura® High-Fidelity Polymerase). In some embodiments, the DNA polymerase is a fast-start polymerase (e.g., FastStart™ Taq DNA polymerase or FastStart™ High Fidelity DNA polymerase).

The amplification reaction mixture will also comprise nucleotides. Nucleotides for use in the methods described herein can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin). In some embodiments, the nucleotides are deoxynucleoside triphosphates ("dNTPs," e.g., dATP, dCTP, dGTP, dTTP, dITP, dUTP, α-thio-dNITs, biotin-dUTP, fluorescein-dUTP, digoxigenin-dUTP, or 7-deaza-dGTP). dNTPs are also well known in the art and are commercially available. In some embodiments, the nucleotides do not comprise dUTP.

In some embodiments, the amplification reaction mixture comprises one or more buffers or salts. A wide variety of buffers and salt solutions and modified buffers are known in the art. For example, in some embodiments, the buffer is TRIS, TRICINE, BIS-TRICINE, HEPES, MOPS, TES, TAPS, PIPES, or CAPS. In some embodiments, the salt is potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, or lithium acetate. In some embodiments, the amplification reaction mixture comprises a salt (e.g., potassium chloride) at a concentration of about 10 mM to about 100 mM.

In some embodiments, the amplification reaction mixture comprises one or more optically detectable agents such as a fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. In some embodiments, the agent is a fluorophore. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836- 850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.,* 40: 83-114 (1971); Stryer, L. *Ann. Rev. Biochem.,* 47: 819-846 (1978); Wang et al., *Tetrahedron Letters* 31: 6493-6496 (1990); Wang et al., *Anal. Chem.* 67: 1197-1203 (1995). Non-limiting examples of fluorophores include cyanines, fluoresceins (e.g., 5'-carboxyfluorescein (FAM), Oregon Green, and Alexa 488), HEX, rhodamines (e.g., N,N,N',N'-tetramethyl-6-carboxyrhodamine (TAMRA), tetramethyl rhodamine, and tetramethyl rhodamine isothiocyanate (TRITC)), eosin, coumarins, pyrenes, tetrapyrroles, arylmethines, oxazines, polymer dots, and quantum dots.

In some embodiments, the detectable agent is an intercalating agent. Intercalating agents produce a signal when intercalated in double stranded nucleic acids. Exemplary intercalating agents include e.g., 9-aminoacridine, ethidium bromide, a phenanthridine dye, EvaGreen, PICO GREEN (P-7581, Molecular Probes), EB (E-8751, Sigma), propidium iodide (P-4170, Sigma), Acridine orange (A-6014, Sigma), thiazole orange, oxazole yellow, 7-aminoactinomycin D (A-1310, Molecular Probes), cyanine dyes (e.g., TOTO, YOYO, BOBO, and POPO), SYTO, SYBR Green I (U.S. Pat. No. 5,436,134: N',N'-dimethyl-N-[4-[(E)-(3-methyl-1,3-benzothiazol-2-ylidene)methyl]-1-phenylquinolin-1-ium-2-yl]-N-propylpropane-1,3-diamine), SYBR Green II (U.S. Pat. No. 5,658,751), SYBR DX, OliGreen, CyQuant GR, SYTOX Green, SYTO9, SYTO10, SYTO17, SYBR14, FUN-1, DEAD Red, Hexidium Iodide, ethidium bromide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, LDS 751 (U.S. Pat. No. 6,210,885), and the dyes described in dyes described in Georghiou, Photochemistry and Photobiology, 26:59-68, Pergamon Press (1977); Kubota, et al., Biophys. Chem., 6:279-284 (1977); Genest, et al., Nuc. Ac. Res., 13:2603-2615 (1985); Asseline, EMBO J., 3: 795-800 (1984); Richardson, et. al., U.S. Pat. No. 4,257,774; and Letsinger, et. al., U.S. Pat. No. 4,547,569.

In some embodiments, the agent is a molecular beacon oligonucleotide probe. As described above, the "beacon probe" method relies on the use of energy transfer. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched.

In some embodiments, the amplification reaction mixture comprises one or more stabilizers. Stabilizers for use in the methods described herein include, but are not limited to, polyol (glycerol, threitol, etc.), a polyether including cyclic polyethers, polyethylene glycol, organic or inorganic salts, such as ammonium sulfate, sodium sulfate, sodium molybdate, sodium tungstate, organic sulfonate, etc., sugars, polyalcohols, amino acids, peptides or carboxylic acids, a quencher and/or scavenger such, as mannitol, glycerol, reduced glutathione, superoxide dismutase, bovine serum albumin (BSA) or gelatine, spermidine, dithiothreitol (or mercaptoethanol) and/or detergents such as TRITON® X-100 [Octophenol(ethyleneglycolether)], THESIT® [Polyoxyethylene 9 lauryl ether (Polidocanol $C_{12}E_9$)], TWEEN® (Polyoxyethylenesorbitan monolaurate 20, NP40) and BRIJ®-35 (Polyoxyethylene23 lauryl ether).

In some embodiments, the concentrated sample and PCR reaction components are partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. Methods of emulsion formation are described, for example, in published patent applications WO 2011/109546 and WO 2012/061444, the entire content of each of which is incorporated by reference herein.

In some embodiments, the droplet is formed by flowing an oil phase through an aqueous sample comprising the concentrated sample and reaction components. The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules may behave as bioreactors able to retain their contents through an incubation period. See, e.g., U.S. Pat. No. 10,378,048. The conversion to microcapsule form may occur upon heating. For example, such conversion may occur at a temperature of greater than about 40°, 50°, 60°, 70°, 80°, 90°, or 95° C. During the heating process, a fluid or mineral oil overlay may be used to prevent evaporation. Excess continuous phase oil may or may not be removed prior to heating. The biocompatible capsules may be resistant to coalescence and/or flocculation across a wide range of thermal and mechanical processing. Following conversion, the microcapsules may be stored at about −70°, −20°, 0°, 3°, 4°, 5°, 6°, 7°, 8°, 9°, 10°, 15°, 20°, 25°, 30°, 35°, or 40° C.

The microcapsule partitions, which may contain one or more polynucleotide sequences and/or one or more one or more sets of primers, may resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions may be incubated per mL. In some embodiments, the sample-probe incubations occur in a single well, e.g., a well of a microtiter plate, without inter-mixing between partitions. The microcapsules may also contain other components necessary for the incubation.

In some embodiments, a sample (e.g., a sample comprising RNA and/or RT-PCR reaction components) is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL. In some embodiments, the droplets have an average volume of about 50 picoliters to about 2 nanoliters. In some embodiments, the droplets have an average volume of about 0.5 nanoliters to about 50 nanoliters. In some embodiments, the droplets have an average volume of about 0.5 nanoliters to about 2 nanoliters.

In some embodiments, the amplification reaction is a droplet digital PCR reaction. Methods for performing PCR in droplets are described, for example, in US 2014/0162266, US 2014/0302503, and US 2015/0031034, the contents of each of which is incorporated by reference. In some embodiments, the QX200 Droplet Digital PCR (ddPCR) System (Bio-Rad) is used.

In some embodiments, a detection reagent or a detectable label in the partitions can be detected using any of a variety of detector devices. Exemplary detection methods include optical detection (e.g., fluorescence, or chemiluminescence). As a non-limiting example, a fluorescent label can be detected using a detector device equipped with a module to generate excitation light that can be absorbed by a fluorophore, as well as a module to detect light emitted by the fluorophore.

In some embodiments, the detector further comprises handling capabilities for the partitioned samples (e.g., droplets), with individual partitioned samples entering the detector, undergoing detection, and then exiting the detector. In some embodiments, partitioned samples (e.g., droplets) can be detected serially while the partitioned samples are flowing. In some embodiments, partitioned samples (e.g., droplets) are arrayed on a surface and a detector moves relative to the surface, detecting signal(s) at each position containing a single partition. Examples of detectors are provided in WO 2010/036352, the contents of which are incorporated herein by reference. In some embodiments, detectable labels in partitioned samples can be detected serially without flowing the partitioned samples (e.g., using a chamber slide).

Following acquisition of fluorescence detection data, a general purpose computer system (referred to herein as a "host computer") can be used to store and process the data. A computer-executable logic can be employed to perform such functions as subtraction of background signal, assignment of target and/or reference sequences, and quantification of the data. A host computer can be useful for displaying, storing, retrieving, or calculating concentration of RNA in the original or concentrated sample; storing, retrieving, or calculating raw data from the nucleic acid detection; or displaying, storing, retrieving, or calculating any sample or source information useful in the methods.

The host computer can be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, can be included. Where the host computer is attached to a network, the connections can be provided via any suitable transport media (e.g., wired, optical, and/or wireless media) and any suitable communication protocol (e.g., TCP/IP); the host computer can include suitable networking hardware (e.g., modem, Ethernet card, WiFi card). The host computer can implement any of a variety of operating systems, including UNIX, Linux, Microsoft Windows, MacOS, or any other operating system.

Computer code for implementing aspects of the present invention can be written in a variety of languages, including PERL, C, C++, Java, JavaScript, VB Script, AWK, or any other scripting or programming language that can be executed on the host computer or that can be compiled to execute on the host computer. Code can also be written or distributed in low level languages such as assembler languages or machine languages.

Scripts or programs incorporating various features of the present invention can be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

Any RNA targets of interested can be detected by the methods described herein. IN some embodiments, the RNA is from a pathogen or non-pathogen. Exemplary pathogens or non-pathogens can be a virus, bacteria or fungus. Exemplary RNA viruses that can be detected include, but are not limited to coronaviruses (e.g., SARS-CoV-2), orthomyxoviruses, Hepatitis C Virus (HCV), Ebola disease, SARS, influenza, polio measles and retrovirus including adult Human T-cell lymphotropic virus type 1 (HTLV-1) and human immunodeficiency virus (HIV).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting RNA in wastewater, the method comprising
    providing a sample comprising RNA in wastewater;
    concentrating RNA in the sample at least 100 fold to form a concentrated sample, wherein the concentrating removes particulates from the sample;
    dividing the concentrated sample into a plurality of partitions;
    performing reverse transcription polymerase chain reaction (RT-PCR) in the plurality of partitions to amplify target RNA, if present, to generate an amplified cDNA;
    detecting the presence or absence of amplified cDNA in the plurality of partitions, wherein the method does not comprise RNA extraction.

2. The method of claim 1, further comprising quantifying the target RNA in the wastewater based on the number of partitions containing detected amplified cDNA.

3. The method of claim 1, wherein the concentrating comprises concentration using tangential flow.

4. The method of claim 3, wherein the tangential flow comprises flowing the sample by hollow fiber filters and extracting captured particles with a foamed wash buffer.

5. The method of claim 1, wherein the plurality of partitions are droplets.

6. The method of claim 1, wherein the plurality comprises at least 1000 partitions.

7. The method of claim 1, wherein the plurality of partitions comprise a fluorescent probe that specifically hybridizes to the amplified cDNA during the detecting.

8. The method of claim 7, wherein the fluorescent probe is an intercalating dye.

9. The method of claim 7, wherein the fluorescent probe is a hydrolysis probe or a molecular beacon.

10. The method of claim 1, wherein the plurality of partitions are microwells.

* * * * *